(12) United States Patent
Yasutomi et al.

(10) Patent No.: US 7,524,675 B2
(45) Date of Patent: Apr. 28, 2009

(54) PHARMACEUTICAL USE OF ALPHA ANTIGEN OR ALPHA ANTIGEN GENE

(75) Inventors: Yasuhiro Yasutomi, Tsu (JP); Hitoshi Mizutani, Tsu (JP)

(73) Assignee: Maruho Co., Ltd., Osaka (JP)

(*) Notice: Subject to any disclaimer, the term of this patent is extended or adjusted under 35 U.S.C. 154(b) by 0 days.

(21) Appl. No.: 11/352,342

(22) Filed: Feb. 13, 2006

(65) Prior Publication Data

US 2006/0153880 A1    Jul. 13, 2006

Related U.S. Application Data

(62) Division of application No. 10/468,456, filed as application No. PCT/JP02/01459 on Feb. 20, 2002, now abandoned.

(30) Foreign Application Priority Data

Feb. 20, 2001  (JP) .............................. 2001-043291

(51) Int. Cl.
C12N 15/00 (2006.01)
A61K 31/711 (2006.01)
C07H 21/04 (2006.01)

(52) U.S. Cl. ...................... 435/320.1; 514/44; 536/23.7
(58) Field of Classification Search ........................ None
See application file for complete search history.

(56) References Cited

U.S. PATENT DOCUMENTS 6,498,148 B1 * 12/2002 Raz .............................. 514/44

FOREIGN PATENT DOCUMENTS

| DE | 4422859 A1 | 1/1996 |
|---|---|---|
| EP | 400973 | 5/1990 |
| JP | 2-308793 | 12/1990 |
| WO | WO 98/26790 | 6/1998 |
| WO | WO 98/44096 | 10/1998 |

OTHER PUBLICATIONS

Mason et al, Molecular Endocrinology 8(3): 325-332, 1994.*
Alm et al, Allergy 53(5): 537, May 1998.*
Dalton et al, J Royal Society of Med 91: 133-134, 1998.*
Spiegelberg et al, Pediatr Pulmonol Suppl 18: 118-21, 1999.*
Fujieda et al, Am J Repir Crit Care Med 160: 2056-206, 1999.*
Raz et al, Proc Natl Acad Sci USA 93: 5141-5145, May 1996.*
Lozes et al, Vaccine 15(8): 830-833, 1997.*
Kline et al, J Immunology 160: 2555-2559, 1998.*
Lozes et al, Vaccine 15(6): 830-833, 1997.*
Verma et al, Nature 389: 239-242, Sep. 1997.*
Reyes-Sandoval et al, Curr Mol Med 1(2):217-43, May 2001.*

(Continued)

*Primary Examiner*—Phuong Huynh
(74) *Attorney, Agent, or Firm*—Sughrue Mion, PLLC

(57) ABSTRACT

The α antigen-encoding gene and the α antigen protein suppress the production of interleukin-4 etc., improve the Th2 type cytokine-dominant state, and furthermore inhibit various conditions of allergic diseases such as IgE production, histamine release and eosinophil infiltration, and therefore they are very effective for the prevention or treatment of atopic diseases such as atopic dermatitis, asthma, allergic rhinitis, and allergic conjunctivitis, and more broadly allergic diseases.

3 Claims, 7 Drawing Sheets

OTHER PUBLICATIONS

Tuteja et al, Crit Rev Biochem Mol Biol 34(1):1-24, 1999.*
Thomas et al, Nature Reviews 4: 346-358, May 2003.*
D. Jullien, et al, "Alpha Interferon Treatment in Atopic Dermatitis", Acta Derm Venereol (Stockh), 73, pp. 130-132 (1993).
B. Windelborg Nielsen, et al, "Interferon therapy for atopic dermatitis reduces basophil histamine release, but does not reduce serum IgE or eosinophilic proteins", Allergy, 49, pp. 120-128 (1994).
H. Tasaka, et al, "Specificity and Distribution of Alpha Antigens of *Mycobacterium Kansasii* and *Mycobacterium marinum*" Am. Reo. Respire. Dis., 130, pp. 647-649 (1984).
H. Tasaka, et al, Specificity and Distribution of Alpha Antigens of *Mycobacterium avium-intracellulare, Mycobacterium scrofulaceum*, and Related Species of Mycobacteria, Am. Reo. Respir. Dis., 132, pp. 173-174 (1985).
H. Kitaura, et al, "Cloning, Sequencing and Expression of the Gene for Antigen from *Mycobacterium Intracellulare* and use of PCR for the Rapid Identification of *Mycobacterium Intracellulare*", Biochemical and Biophysical Research Communications, vol. 196, No. 3, pp. 1466-1473 (1993).
C.E.H. Grattan, et al, "Randomized double-blind study of cyclosporin in chronic 'idiopathic' urticaria", British Journal of Dermatology, 143, pp. 365-372 (2000).
K. M. McAveney, et al, "Induction of THI- and TH2-associated cytokine mRNA in mouse bladder following intravesical growth of the murine bladder tumor MB49 and BCG immunotherapy", Cancer Immunol Immunother, 39, pp. 401-406 (1994).
A. Thanhäuser, et al, "The induction of bacillus-Calmette-Guérin-activated killer cells requires the presence of monocytes and T-helper type-1 cells", Cancer Immunol Immunother, 40, pp. 103-108 (1995).
H. Niwa, et al, Efficient selection for high-expression transfectants with a novel eukaryotic vecotr, Gene, 108, pp. 193-200 (1991).
H. Tasaka, et al, "Purification and Antigenic Specificity of Alpha Protein (Yoneda and Fukui) from *Mycobacterium tuberculosis* and *Mycobacterium intracellulare*", Hiroshima Journal of Medical Sciences, vol. 32, No. 1, pp. 1-8 (1983).
M. Borremans, et al, "Cloning, Sequence Determination, and Expression of a 32-Kilodalton-Protein Gene of *Mycobacterium tuberculosis*", Infection and Immunity, vol. 57, No. 10, pp. 3123-3130 (1989).
K. Matsuo, et al, "Cloning and Expression of the Gene for the Cross-Reactive a Antigen of *Mycobacterium kansaii*", Infection and Immunity, vol. 58, No. 2, pp. 550-556 (1990).
J. Content, et al, "The Genes Coding for the Antigen 85 Complexes of *Mycobacterium tuberculosis* and *Mycobacterium bovis* BCG are Members of a Gene Family: Cloning, Sequence Determination, and Genomic Organization of the Gene Coding for Antigen 85-C of *M. tuberculosis*", Infection and Immunity, vol. 59, No. 9, pp. 3205-3212 (1991).
K. Huygen, et al, "Spleen Cell Cytokine Secretion in *Mycobacterium bovis* BCG-Infected Mice", Infection and Immunity, vol. 60, No. 7, pp. 2880-2886 (1992).
N. Ohara, et al, "Cloning and Sequencing of the Gene for a Antigen from *Mycobacterium avium* and Mapping of B-Cell Epitopes", Infection and Immunity, vol. 61, No. 4, pp. 1173-1179 (1993).
A. Mori, et al, "Control of IL-5 production by human helper T cells as a treatment for eosinophilic inflammation: Comparison of in vitro and in vivo effects between selective and nonselective cytokine synthesis inhibitors", J. Allergy Clin Immunol, vol. 106, No. 1, Part 2, pp. S58-S64 (2000).
A. Torrelo, et al, "Interferon therapy for chronic urticaria", Journal of the American Academy of Dermatology, vol. 32, No. 4, pp. 684-685 (1991).
K. Matsuo, et al, "Cloning and Expression of the *Mycobacterium bovis* BCG Gene for Extracellular a Antigen", Journal of Bacteriology, vol. 170, No. 9, pp. 3847-3854 (1988).
K. Yamanaka, et al, "Skin-Specific Caspase-l-Transgenic Mice Show Cutaneous Apoptosis and Pre-Endotoxin Shock Condition with a High Serum Level of IL-18", The Journal of Immunology, vol. 165, pp. 997-1003 (2000).
H. G. Wiker, et al, "The Antigen 85 Complex: a Major Secretion Product of *Mycobacterium tuberculosis*", Microbiological Reviews, vol. 56, No. 4, pp. 648-661 (1992).
J. E. R. Thole, et al, "Molecular and immunological analysis of a fibronectin-binding protein antigen secreted by *Mycobacterium leprae*", Molecular Microbiology, 6(2), pp. 153-163 (1992).
T. Yoshimoto, et al, "IL-18 induction of IgE: dependence on CD4 T cells, IL-4 and STAT6", Nature Immunology, vol. 1, No. 2, pp. 132-137 (2000).
Editorial "Taming tuberculosis—again", Nature Structural Biology, vol. 7, No. 2, pp. 87-88 (2000).
M. Furue, "Cytokine, Adhesion Molecules and Cutaneous Lymphocyte-Associated Antigen in Atopic Dermatitis", Progress in Medicine, vol. 17, No. 1, pp. 19-24 (1997).
N. Wada, et al, "Long-Lasting Immune Response Induced by Recombinant Bacillus Calmette-Guérin (BCG) Secretion System", Scand. J. Immunol. 43, pp. 202-209 (1996).
J. T. Belisle, et al, "Role of the Major Antigen of *Mycobacterium tuberculosis* in Cell Wall Biogenesis", Science, vol. 276, pp. 1420-1422 (1997).
T. Mastsunaga, et al, "Current conception of topic dermititas", Igaku no Ayumi (Journal of Clinical and Experimental Medicine), 180(1), pp. 51-55 (1997).
C. B. Scanga, et al, "Development of an Asthma Vaccine—Research into BCG", Drugs, 59(6); pp. 1217-1221 (2000).
M. Kumar, et al, "A recombinant BCG vaccine generates a Th1-like response and inhibits IgE synthese in BALB/c mice", Immunology, 97, pp. 515-521 (1999).
P. D. Arkwright, et al, "Intradermal administration of a killed Mycobacterium vaccae suspension (SRL 172) is associated with improvement in atopic dermatitis in children with moderate-to-severe disease", J Allergy Clin Immunol, vol. 107, No. 3, pp. 531-534 (2001).
Ngo et al, The Protein Folding Problem and Tertiary Structure Prediction, pp. 491-495 (1994).
Stryer et al, in Biochemistry, Third Edition, W H Freeman Company, New York, pp. 31-33 (1998).
Naito et al, Vaccine 18: 795-798, Jan. 2000.
Launois et al, Infection and Immunity 62(9):3679-3687, Sep. 1994.
Webster's II New Riverside University Dictionary, p. 933 (1984).
European Search Report dated Jan. 4, 2008.
C.C. Wang, et al., "Inhibition of an established allergic response to ovalbumin in BALB/c mice by killed Mycobacterium vaccae", Immunology, 93: 307-313, 1998.
Erika von Mutius, et al., "International patterns of tuberculosis and the prevalence of symptoms of asthma, rhinitis, and eczema", Thorax, 55(6): 449-453, 2000.

* cited by examiner

FIG. 6
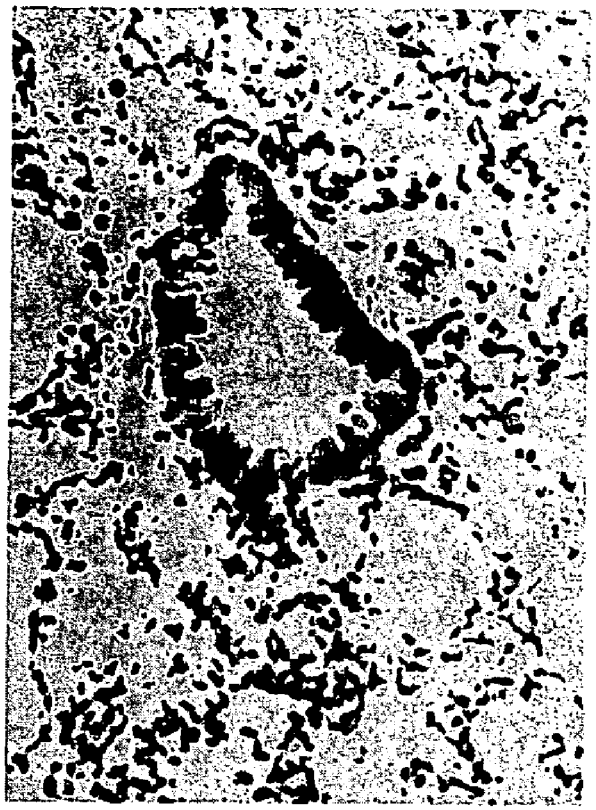
α ANTIGEN ADMINISTRATION
NO TREATMENT

FIG. 7
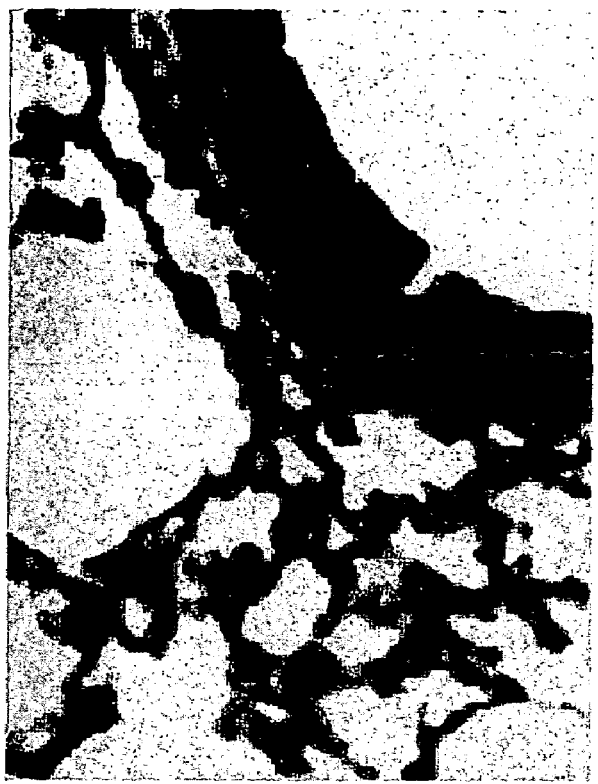
α ANTIGEN ADMINISTRATION
NO TREATMENT

SEQUENCE LISTING

```
<160> NUMBER OF SEQ ID NOS: 2

<210> SEQ ID NO 1
<211> LENGTH: 1396
<212> TYPE: DNA
<213> ORGANISM: Mycobacterium kansasii

<400> SEQUENCE: 1
gttaactatt ctttgtaccg ctccccgcct gccgccttct gccctgctcc gggtgcatag      60
cacccgtttg cgctccggat tatccgggcc gcaacggggc aacgggggaa gcggtggagt     120
ccgtcgccga ctcgcatagc accgttgctg tgttggcggg ggtaaccgat atcgaaatgg     180
aatgacttcg cgtcccgatc gacatttgcc ctactcacac ggtaagttct gccgggagca     240
cgcgagcaca tacggacaag gggcagggta tgacagacgt gagcgggaag attcgggcgt     300
ggggccgacg ccttctggtc ggcgcggccg ctgctgcggc ccttcctggc ctggtcggac     360
tcgccggcgg agcggcgacc gcgggagcgt tctcccgtcc cggcctgccg gtggagtacc     420
tccaggtgcc gtcggctgcg atgggtcgca gtatcaaggt tcaattccaa agtggcgggg     480
acaactcgcc ggcggtgtac ctgctcgacg gtctccgcgc tcaagacgac tacaacggct     540
gggacatcaa caccccggcc ttcgagtggt actaccaatc gggcctgtcg gtcatcatgc     600
cggtcggcgg acagtccagt ttctacagtg actggtacag cccggcctgc ggcaaggccg     660
gctgcacgac ctacaagtgg gagaccttcc tgaccagcga gctgccgcaa tggctgtccg     720
cgaaccggag tgtcaagccc accggaagcg ccgcggtcgg catctcgatg gccggctcgt     780
cggccctgat cctgtccgtc taccacccgc agcagttcat ctacgcgggt tcgttgtcgg     840
ccctgatgga cccctcccag gggatggggc cgtctctgat cggcttggcg atgggtgacg     900
ccggtggtta caaggcctcg gacatgtggg gaccctcgag tgacccagcc tggcagcgta     960
acgacccgtc gctgcacatt ccggagctgg tcgccaacaa cacccgcctg tggatctact    1020
gcggcaacgg caccccgtcc gagttgggcg gtgccaatgt tccggccgaa ttcctggaga    1080
acttcgttcg cagcagcaac ctgaaattcc aggacgccta caacgccgcg ggcggccaca    1140
acgccgtgtt caatttggac gccaacggaa cgcacagctg ggagtactgg ggcgcgcagc    1200
tcaacgccat gaagggtgac ctgcaggcca gcctgggcgc ccgctgatcg cgcaacggtt    1260
gccgctactg ggcttgacgg caagacgccg tcaagccagt agtgtgttcg gcaccttgaa    1320
cgctggtccg ccatgttcaa cgagccggtc tacctgcccg caccgaacaa gctggtgaca    1380
tcgacccatg cggtgc                                                    1396

<210> SEQ ID NO 2
<211> LENGTH: 285
<212> TYPE: PRT
<213> ORGANISM: Mycobacterium kansasii

<400> SEQUENCE: 2

Phe Ser Arg Pro Gly Leu Pro Val Glu Tyr Leu Gln Val Pro Ser Ala
1               5                   10                  15

Ala Met Gly Arg Ser Ile Lys Val Gln Phe Gln Ser Gly Gly Asp Asn
            20                  25                  30
```

-continued

```
Ser Pro Ala Val Tyr Leu Leu Asp Gly Leu Arg Ala Gln Asp Asp Tyr
        35                  40                  45

Asn Gly Trp Asp Ile Asn Thr Pro Ala Phe Glu Trp Tyr Tyr Gln Ser
    50                  55                  60

Gly Leu Ser Val Ile Met Pro Val Gly Gly Gln Ser Ser Phe Tyr Ser
65                  70                  75                  80

Asp Trp Tyr Ser Pro Ala Cys Gly Lys Ala Gly Cys Thr Thr Tyr Lys
            85                  90                  95

Trp Glu Thr Phe Leu Thr Ser Glu Leu Pro Gln Trp Leu Ser Ala Asn
                100                 105                 110

Arg Ser Val Lys Pro Thr Gly Ser Ala Ala Val Gly Ile Ser Met Ala
        115                 120                 125

Gly Ser Ser Ala Leu Ile Leu Ser Val Tyr His Pro Gln Gln Phe Ile
        130                 135                 140

Tyr Ala Gly Ser Leu Ser Ala Leu Met Asp Pro Ser Gln Gly Met Gly
145                 150                 155                 160

Pro Ser Leu Ile Gly Leu Ala Met Gly Asp Ala Gly Gly Tyr Lys Ala
            165                 170                 175

Ser Asp Met Trp Gly Pro Ser Ser Asp Pro Ala Trp Gln Arg Asn Asp
                180                 185                 190

Pro Ser Leu His Ile Pro Glu Leu Val Ala Asn Asn Thr Arg Leu Trp
            195                 200                 205

Ile Tyr Cys Gly Asn Gly Thr Pro Ser Glu Leu Gly Gly Ala Asn Val
        210                 215                 220

Pro Ala Glu Phe Leu Glu Asn Phe Val Arg Ser Ser Asn Leu Lys Phe
225                 230                 235                 240

Gln Asp Ala Tyr Asn Ala Ala Gly Gly His Asn Ala Val Phe Asn Leu
            245                 250                 255

Asp Ala Asn Gly Thr His Ser Trp Glu Tyr Trp Gly Ala Gln Leu Asn
            260                 265                 270

Ala Met Lys Gly Asp Leu Gln Ala Ser Leu Gly Ala Arg
        275                 280                 285
```

PHARMACEUTICAL USE OF ALPHA ANTIGEN OR ALPHA ANTIGEN GENE

CROSS-REFERENCE TO RELATED APPLICATION

This Application is a Divisional of U.S. application Ser. No. 10/468,456, filed Aug. 20, 2003 and now abandoned, which is a 371 of PCT/JP02/01459, filed Feb. 20, 2002, the disclosures of each of which are incorporated herein by reference.

TECHNICAL FIELD

The present invention relates to novel pharmaceutical uses of α antigen derived from acid-fast bacteria (*Mycobacteria*) or analogs thereof or genes encoding them. More specifically, it relates to novel pharmaceutical uses of α antigen derived from *Mycobacterium kansasii* or analogs thereof or expression vectors containing a gene encoding them for the prevention or treatment of allergic diseases such as atopic dermatitis, asthma, allergic rhinitis and allergic conjunctivitis.

BACKGROUND ART

Allergic diseases such as atopic dermatitis, asthma, allergic rhinitis and allergic conjunctivitis are diseases in which hypersensitive reactions occur against environmental antigens to which normal healthy people do not react and destruction and disorders of various organs occur due to the autoimmune system. As an onset mechanism of these diseases, there has been considered the enhanced allergic reactions caused by Th2 type cytokines such as interleukin-4 and interleukin-5 that the Th2 cells among the Th differentiate involved in cellular immune responses against antigen (Progress in Medicine 17: 19-20, 1997) The elucidation of the induction mechanism and the control mechanism has important physiological and pharmacological implications, but detailed mechanisms thereof have yet to be clarified. Therapies of these diseases in current use include evasion from antigen, the control of non-specific inflammatory reactions by the oral administration of antihistamines that antagonize the binding of mediators such as histamine to receptors and by topical steroid (Igaku No Ayumi (Journal of Clinical and Experimental Medicine) 180: 51-55, 1997).

For the treatment of allergic diseases, there can be conceived the suppression of allergic reactions by shifting the Th2 type cytokine-dominant allergic state to the Th1 type cytokine-dominant state, and since interferon-γ produced by Th1 cells suppresses the effect of enhancing IgE production by interleukin-4 produced by Th2 cells (Progress in Medicine 17: 19-20, 1997), interferon-γ has been in trial use for the treatment of allergic diseases (J. Am. Acad. Dermatol. 32: 684-685, 1991; Allergy 49: 120-128, 1994; Acta Derm. Venereol 73: 130-132, 1993), but the effect is small and the results have not been satisfactory, and thus has not been subjected to clinical uses.

For the establishment of atopic diseases, the maintenance of the Th2 type-dominant immunological state and the maintenance of ensuing inflammatory reactions are involved. For the improvement of the Th2 type-cytokine dominant immunological state, control of cytokines by immunosupprresive agents has been attempted (Br. J. Dermatol. 143: 365-72, 2000; J. Allergy Clin. Immunol. 106 (1 pt2): S58-64, 2000), but that did not lead to the essential improvement of the immunological state and thereby had a limited effect.

On the other hand, BCG vaccine is a vaccine that utilizes an attenuated strain of *Mycobacterium bovis* and is the only live vaccine approved for *Mycobacterium tuberculosis* infections. BCG vaccine has a potent adjuvant effect with little side effects, and thus has been given to many people in the world today as a safe vaccine. Now, BCG vaccine has been reported to have an activity of shifting CD4+ helper T cells to Th1 cells that are responsible for cell-mediated immunity by producing interferon-γ and interleukin-2 (Cancer Immunol. Immunother. 39: 401-406, 1994; ibid. 40: 103-108, 1995).

As a protein that is omnipresent among *Mycobacteria*, the antigen 85 complex was identified. The protein complex is composed of an antigen 85 complex-forming protein 85A with a molecular weight of about 30-32 kd (Infect. Immun. 57:3123-3130, 1989), an antigen 85 complex-forming protein 85B (J. Bacteriol. 170: 3847-3854, 1988) and an antigen 85 complex-forming protein 85C (Infect. Immun. 59: 3205-3212, 1991), which are major secretory proteins of *Mycobacteria*. These secretory proteins exhibit high homology of the gene sequence and the amino acid sequence and cross reactivity to monoclonal antibodies among the bacteria of the same genera such as *Mycobacterium tuberculosis, Mycobacterium bovis, Mycobacterium kansasii* etc. irrespective of the species (Microbiol. Rev. 56: 648-661, 1992) and have, as common functions, the activity of binding to fibronectin and of mycolyl group transferase in the cell wall synthesis (Microbiol. Rev. 56: 648-661, 1992; Science 276: 1420-1422, 1997; Nat. Struct. Biol. 7: 887-88, 2000). Among these secretory proteins, the antigen 85 complex-forming protein 85B is widely known as α antigen.

Currently, furthermore, α antigen has been isolated and purified as a tuberculin reactive protein from the culture supernatant of *Mycobacterium tuberculosis*, and it has been revealed, there is an epitope in the molecule (Am. Rev. Respir. Dis. 130: 647-649, 1984; ibid. 132: 173-174, 1985 ; Microbiological Reviews 56: 648-661, 1992), and it has been reported that this α antigen has the above-mentioned effect of shifting to the Th1 cells (Infect. Immun. 60: 2880-2886, 1992). Attempts have also been made to use and improve Bacillus Calmette-Guerin by recombinant DNA technology, and then to use as a vaccine to various pathogens. For example, it has been reported, an expression vector was constructed in which a gene encoding the surface antigen of AIDS virus was integrated into the gene containing the a antigen, and the vector was used to transform Bacillus Calmette-Guerin, which transformant is used as a BCG vaccine (WO 96/4009).

Up until today, however, no attempts have been made to use a gene encoding the α antigen or the α antigen per se for the treatment of allergic diseases. Furthermore, though the α antigen has been reported to have the effect of shifting CD4+ helper T cells to Th1 cells, it is not yet clear whether the α antigen or the α antigen gene is effective for the prevention or treatment of allergic diseases such as atopic dermatitis and asthma for which the mechanism of onset has not been elucidated. In addition, as described above, though the shifting of the Th1 type/Th2 type balance to the Th2 type-dominant state is considered to be important for the establishment of allergic diseases, no reports have been made so far that the mere shifting to the Th1 cell side led to the improvement of skin conditions of atopic dermatitis.

DISCLOSURE OF THE INVENTION

Thus, it is an object of the present invention to provide novel pharmaceutical use of the *Mycobacterium*-derived α antigen such as BCG bacteria or analogs thereof or genes encoding them for the prevention or treatment of allergic diseases.

The present inventors have found that when an expression vector containing the α antigen-coding gene is applied to Caspase-1 transgenic mice, a mouse model which is at the Th2 type cytokine-dominant immunological state and which has a persistent atopic dermatitis-like dermatitis, the production of interleukin-4 was inhibited, blood levels of histamine and IgE were also suppressed, and skin diseases were improved, indicating that atopic dermatitis can be healed. The α antigen protein was also found to heal atopic dermatitis in a similar manner. Furthermore, when an expression vector containing the α antigen-coding gene was applied to a mouse asthma model, it was found, IgE production was inhibited and allergic conditions such as eosinophil-infiltration can be improved, leading to the healing of asthma. Thus, the present inventors have revealed that the α antigen gene or the α antigen protein improves the Th2 type cytokine-dominant immunological state and can suppress and/or improve various conditions of allergic diseases, and thus is widely effective for the prevention or treatment of allergic diseases, and thereby have completed the present invention.

Thus, the present invention relates to a pharmaceutical composition for the prevention or treatment of allergic diseases comprising, as an active ingredient, the *Mycobacterium*-derived α antigen, an analog thereof, a mutant thereof having a function similar thereto, or a gene encoding them.

Furthermore, the present invention relates to a method of preventing or treating allergic diseases, said method comprising administering an effective amount of the *Mycobacterium*-derived α antigen, an analog thereof, a mutant thereof having a function similar thereto, or a gene encoding them to mammals including humans.

Furthermore, the present invention relates to the use of the *Mycobacterium*-derived α antigen, an analog thereof, a mutant thereof having a function similar thereto, or a gene encoding them for the production of a pharmaceutical composition for the prevention or treatment of allergic diseases.

According to a preferred embodiment, the present invention uses an expression vector encoding the *Mycobacterium*-derived α antigen or an analog thereof, or the α antigen protein or an analog protein thereof for the prevention or treatment of atopic diseases such as atopic dermatitis, asthma, allergic rhinitis, and allergic conjunctivitis. As used herein, as analogs of the α antigen, there can be mentioned an antigen 85 complex-forming protein 85A, antigen 85 complex-forming protein 85C and the like.

BRIEF EXPLANATION OF THE DRAWINGS

FIG. 6 is a graph showing the degree of infiltration of eosinophils in the lung tissue when an expression vector containing a gene encoding the α antigen was administered to a mouse asthma model.

FIG. 7 is a graph showing the result of histological examination of the lung when an expression vector containing the gene encoding the α antigen was administered to a mouse asthma model.

BEST MODE FOR CARRYING OUT THE INVENTION

Figure 1:
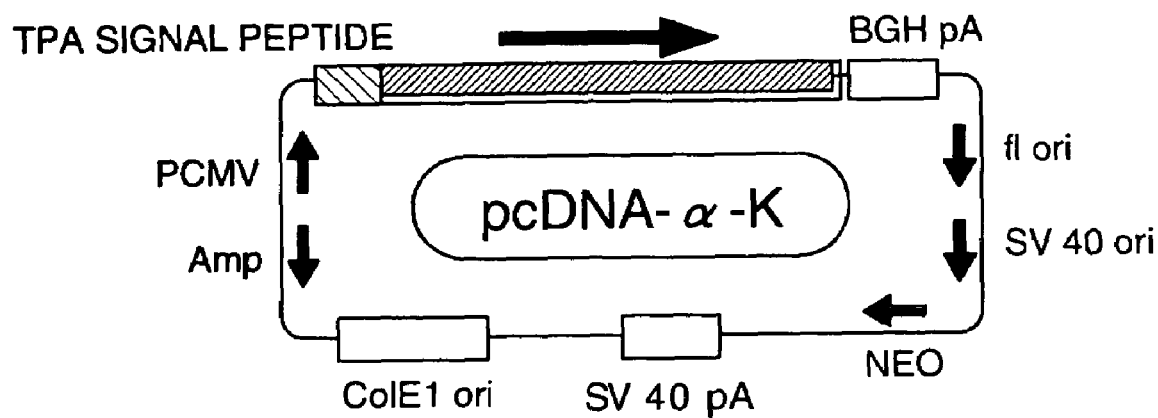
FIG. 1 shows the construction of an expression vector, constructed in Example 1, containing a gene encoding the α antigen for use as an active ingredient of a pharmaceutical composition for the prevention or treatment of allergic diseases of the present invention.

The subject diseases of the present invention are allergic diseases, and more specifically allergic diseases caused by the Th2 type cytokine-dominant state. The preferred subject allergic diseases of the present invention are specifically atopic diseases, for example atopic dermatitis, asthma, allergic rhinitis and allergic conjunctivitis, and specifically atopic dermatitis and asthma.

As used herein, genes encoding the *Mycobacterium*-derived α antigen or an analog thereof refers to genes capable of expressing the α antigen protein, or α antigen protein analogs such as antigen 85 complex-forming protein 85A and antigen 85 complex-forming protein 85C. Specifically, there can be mentioned genes in the form of an expression vector containing a gene encoding the α antigen or an analog thereof. As genes encoding the α antigen, there can be illustrated genes encoding the α antigen derived from Mycobactera such as *Mycobacterium kansasii* (Infect. Immun. 58: 550-556, 1990), *Mycobacterium avium* (Infect. Immun. 61: 1173-1179, 1993), *Mycobacterium* intracellulare (Biochem. Biophys. Res. Commun. 196: 1466-1473, 1993), *Mycobacterium leprae* (Mol. Microbiol. 6: 153-163, 1992) and the like. Any of these genes can be used in the present invention, and as a gene encoding α antigen derived from *Mycobacterium kansasii*, there can be mentioned a DNA having the base sequence from positions 390 to 1244 of SEQ ID NO: 1.

In addition to this DNA, they may be a mutant DNA that hybridizes to this DNA under a stringent condition, or a mutant DNA comprising a DNA encoding a protein having an amino acid sequence in which one or more than one (preferably several) amino acid residues have been substituted, deleted and/or added to the amino acid sequence of the protein encoded by this DNA, wherein said mutant encodes a protein having the same function as the *Mycobacterium kansasii*-derived α antigen. As used herein, as a specific method of obtaining a mutant DNA that hybridizes to this DNA under a stringent condition, there can be mentioned the following method. Thus, a colony hybridization is performed in the presence of 50% formamide, 4× Denhardt, 5×SSPE (SSPE solution: EDTA sodium phosphate (SSPE),1×Denhardt: 0.02% Ficoll, 0.02% polyvinyl pyrrolidone, 0.02% bovine serum albumin), 0.2% SDS, 100 µg/ml ssDNA, and 12.5 ng of a probe (12.5 ng of a purified cDNA fragment having a base sequence from positions 390 to 1244 of SEQ ID NO: 1 labelled with [α-$^{32}$P]dCTP (Amersham) using the BcaBest DNA Labeling kit (TaKaRa)) at 45° C. for 14-16 hours, the filter is washed in 1×SSPE and a 0.5% SDS solution at 45° C./30 min, then in 0.1×SSPE and a 0.5% SDS solution at 55° C./1 hour, and finally 0.1×SSPE and a 0.5% SDS solution at 65° C./1 hour to eliminate the background completely, which is then exposed to an X-ray film (Fuji) at −80° C. for 72 hours to determine the position of and isolate the corresponding colony and thus the mutant DNA can be obtained. The above same function as the α antigen derived from *Mycobacterium kansasii* means to have a similar effect of preventing or treating allergic diseases. These mutants are those for which amino acid sequences encoded thereby usually have a homology of 60% or greater with the amino acid sequence of the α antigen protein, and preferably a homology of 75% or greater. In the case of genes encoding the α antigen other than *Mycobacterium kansasii,* they may be mutants thereof as well.

As genes encoding the antigen 85 complex-forming protein 85A which is an analog of the αantigen, there can be mentioned genes derived from the *Mycobacteria* similar to various *Mycobacteria* described above for the α antigen gene. More specifically, there can be mentioned a DNA encoding the antigen 85 complex-forming protein 85A derived from *Mycobacterium tuberculosis* (Infect. Immun. 57: 3123-3130, 1989). For genes encoding the antigen 85 complex-forming protein 85C as well, there can be mentioned a gene derived from various *Mycobacteria,* and more specifically, there can be mentioned a DNA encoding the antigen 85 complex-forming protein 85C derived from *Mycobacterium tuberculosis* (Infect. Immun. 59: 3205-3212, 1991). For these DNAs as well, as described antibody, they may be a mutant DNA that hybridizes to this DNA under a stringent condition, or a mutant DNA comprising a DNA encoding a protein having an amino acid sequence in which one or more than one (preferably several) amino acid residues have been substituted, deleted and/or added to the amino acid sequence of the protein encoded by this DNA, wherein said mutant encodes a protein having the same function as the antigen 85 complex-forming protein 85A or the antigen 85 complex-forming protein 85C.

The above DNAs can be cloned by a methyl such as RT-PCR reaction on mRNA derived from *Mycobacteria* using as PCR primers appropriate DNA segments based on the sequence information described in the above literature, sequence information of Genebank, etc. Chemical synthesis is also possible based on the amino acid sequence information. Furthermore, the above DNA mutants may be easily obtained using, for example, site-directed mutagenesis, PCR method, a common hybridization method, or the like.

In accordance with the present invention, the α antigen protein derived from *Mycobacteria* or derivatives thereof such as antigen 85 complex-forming protein 85A or antigen 85 complex-forming protein 85C or mutant proteins thereof can be used for the prevention or treatment of allergic diseases. As such α antigens, there can be mentioned proteins encoded by genes encoding the above-mentioned α antigen. Specifically, there can be mentioned an α antigen which is encoded by the DNA having the base sequence derived from *Mycobacterium kansasii* described in SEQ ID NO: 1 and which has the amino acid sequence of SEQ ID NO: 2. In addition to the α antigen having this amino acid sequence, it may be a mutant protein comprising an amino acid sequence in which one or more than one (preferably several) amino acid residues have been substituted, deleted and/or added to the amino acid sequence of SEQ ID NO: 2, said protein having the same function as the α antigen. In the case of the α antigen derived from *Mycobacterium* other than *Mycobacterium kansasii* as well, it may be a mutant protein comprising a protein in which one or more than one (preferably several) amino acid residues have been substituted, deleted and/or added to the amino acid sequence of those amino acid sequences, said protein having the same function as the α antigen. For the antigen 85 complex-forming protein 85A or the antigen 85 complex-forming protein 85C as well, there can be mentioned the antigen 85 complex-forming protein 85A derived from *Mycobacterium tuberculosis* (Infect. Immun. 57: 3123-3130, 1989), the antigen 85 complex-forming protein 85C derived from *Mycobacterium tuberculosis* (Infect. Immun. 59: 3205-3212, 1991) and the like. The analogs of these α antigen proteins may be mutants similar to those of the α antigen protein mentioned above.

These proteins may be produced by a recombinant DNA technology using genes encoding them or by chemical synthesis. Alternatively, *Mycobacteria* such as *Mycobacterium kansasii* may be cultured in a suitable medium, and from the culture liquid, the proteins may be purified by a known purification method (Scand. J. Immunol. 43: 202-209, 1996; J. Bacteriol. 170: 3847-385 4, 1988; Hiroshima J. Med. Sci. 32: 1-8, 1983).

In accordance with the present invention, when genes encoding the *Mycobacterium*-derived α antigen, a derivative thereof, or a mutant thereof are used for the prevention or treatment of allergic diseases, specifically they may be used in the form of an expression vector containing a gene encoding the α antigen, an analog thereof, or a mutant thereof. Expression vectors containing these genes are roughly divided into two: cases when non-virus vectors are used, and cases when virus vectors are used.

Non-virus vectors may be any expression vectors as long as they can express and secrete genes that encode the α antigen, a derivative thereof, or a mutant thereof, and by way of example, there can be mentioned pCAGGS (Gene 108: 193-200, 1991), pBK-CMV, pcDNA3.1, pZeoSV (Invtrigen, Stratagene) etc.

As virus vectors, representative virus vectors include recombinant adenovirus, retrovirus and the like. More specifically, there can be mentioned DNA viruses or RNA viruses such as detoxicated retrovirus, adenovirus, adeno-associated virus, helper virus, vaccinia virus, pox virus, poliovirus, Sindbis virus, Sendai virus, SV40, and human immunodeficiency virus (HIV).

By integrating a gene encoding the α antigen, an analog thereof or a mutant thereof into these vectors, expression vectors can be constructed.

These vectors may be generally administered to mammals including humans in the form of injections depending on the method of introducing into the living body. In the case of virus vectors, they may be administered as they are. Injections may be prepared according to a standard method, and for example after they are dissolved in a suitable solvent (a buffer such as PBS, physiological saline, sterile water etc.), they may be filter-sterilized as desired with a filter etc. and then filled into a sterile container for formulation. Commonly used carriers may be added to the injections, as necessary. They may also be in the form of liposome formulations described below.

In order to use the expression vectors thus obtained for the treatment of allergic diseases, they can be administered in a standard method. Specifically, such methods include, for example, the lipofection method, the phosphate-calcium coprecipitation method, the DEAE-dextran method, the electroporation method, direct DNA injection methods using micro glass capillaries, and the like. Furthermore, there are methods of introducing genes into the tissue. Such methods include, for example, gene introduction with internal type liposomes, gene introduction with electrostatic type liposomes, HVJ-liposome methods, improved HVJ-liposome methods (HVJ-AVE liposome methods), receptor-mediated gene introduction, methods of introducing DNA molecules into the cell together with carriers (metal particles) by a particle gun, in vivo electroporation, and the like. There can also be used a method of dissolving a non-virus vector expression plasmid into physiological saline and using it as it is (the so-called naked-DNA direct introduction), a method of introduction with positively charged polymers, and the like.

When the expression vector is a virus vector, it can be used as it is, or can be administered in the form of an injection as described above.

Expression vectors containing the gene encoding α antigen, an analog thereof or a mutant thereof are usually administered to the skin, muscles, the abdominal cavity etc. of mammals including humans. The dosage may vary depending on the type of the expression vector, dosage form, dosage regimen, the subject patient, type of disease etc., and is generally, as the expression vector, about 0.005 to about 2 mg, preferably about 0.1 mg to about 1 mg, generally once daily over several months for a total of a few times.

In accordance with the present invention, when *Mycobacterium*-derived α antigen protein, an analog protein thereof, or a mutant protein thereof is used as it is, it may generally be administered pareterally, for example intravenously, intramuscularly, intraperitoneally, subcutaneously, topically, etc. When administered parenterally, it may be given in the form of an injection, local application form, etc.

As injections, there can be mentioned sterile solutions, suspensions, or the like. As topical applications, there can be mentioned creams, ointments, lotions, sprays, aerosols, transdermal formulations (common patches, matrices etc.), and the like. These formulations may be prepared by conventional methods in combination with pharmaceutically acceptable excipients, additives etc. As pharmaceutically acceptable excipients and additives, there can be mentioned carriers, binders, flagrants, buffers, thickeners, colorants, stabilizers, emulsifying agents, dispersants, suspending agents, preservatives, and the like.

Specifically, as injections, there can be mentioned solutions, suspensions, and emulsions and the like. For example, the α antigen protein may be added into a PBS buffer, physiological saline, sterile water etc., to which albumin may be added as desired, which is filter-sterilized with a filter etc. and then filled into sterile containers for formulation. They may also be lyophilized and dissolved to prepare injections at the time of administration. Ointments and creams used as topical applications may be formulated by adding the α antigen protein together with a thickener or a gelling agent to an aqueous or oily base. As the base, there can be mentioned for example water, liquid paraffin, plant oils (peanut oil, castor oil, etc.) and the like. As thickeners, there can be mentioned for example soft paraffin, aluminum stearate, cetostearyl alcohol, polyethylene glycol, lanoline, hydrogenated lanoline, beeswax, and the like. Lotions may be formulated in a standard method by adding one or more of pharmaceutically acceptable stabilizers, suspending agents, emulsifying agents, dispersants, thickeners, colorants, flagrants etc. to an aqueous or oily base. Sprays, aerosols, patches, matrices, etc. can also be formulated according to standard methods. These local applications may contain, as desired, preservatives such as methyl hydroxybenzoate, propyl hydroxybenzoate, chloro cresol, and benzalkonium chloride, and bactericidal agents.

The dosage and the number of administration of the α antigen protein, a derivative thereof, or a mutant proteins thereof may vary depending on the symptom, age, body weight, dosage regimen, etc., and when administered as injections, generally about 1 mg to about 10 mg, preferably about 1 mg to about 5 mg is administered once or several times in divided doses. When topically administered, generally about 10 μg of the dose may be administered over several days.

The present invention will now be specifically explained with reference to the following examples, but these examples should not be construed to limit the present invention.

EXAMPLE 1

Effect of an Expression Vector Containing an α Antigen-Encoding Gene on Atopic Dermatitis (1) Construction of Expression Vector By inserting the α antigen gene (α-K) of *Mycobacterium kansasii* comprising the base sequence from positions 390-1244 set forth in SEQ ID NO: 1 into the KpnI-ApaI site of pcDNA3.1 (Invitrogen CA), and then integrating it downstream of the CMV promoter and the TPA signal peptide, an expression vector pcDNA-α-K having the construction shown in FIG. 1 was constructed as an active ingredient of a pharmaceutical composition for the treatment of allergic diseases of the present invention (Infect. Immun. 58: 550-556, 1996).

(2) Administration of an Expression Vector to a Mouse Model of Atopic Dermatitis i) Method Transgenic mice (CTg) that express skin-specific Caspase-1 and that are in the Th2-dominant immunological state were used (J. Immunol. 165: 997-1003, 2000; Nat. Immunol. 1: 132-137, 2000; Proc. Nah. Acod. Sci. USA 99;11340-11345, 2002). These mice developed atopic dermatitis from week 8 after birth.

To CTg mice at week 4, 10 and 12 (4, 10 and 12 week old) after birth, 100 μg of the expression vector constructed in the above (1) dissolved in PBS was intraperitoneally administered. Then, for the 4, 10 and 12 week old CTg mice, at week 8 after the administration, serum levels of histamine and IgE as well as the expression level of interleukin-4 mRNA in the skin were investigated. Levels of histamine and IgE were measured by RIA, and interleukin-4 mRNA by RT-PCR.

ii) Result

The result obtained is shown in Table 1. As can be seen from Table 1, in the CTg mouse group that received the expression vector, no increases in blood levels of IgE or histamine were observed, and were in the normal range. Also, interleukin-4 mRNA in the skin became undetectable. During the observation period, no development of dermatitis or no scratch behavior were seen.

In contrast, no treatment CTg mice developed dermatitis at week 8 and exhibited scratch behavior. Also, blood levels of IgE and histamine were elevated.

TABLE 1

Effect on atopic dermatitis

| Time of administration | Histamine (nM/l) | | IgE level (μg/ml) | | Skin IL-4 mRNA | |
|---|---|---|---|---|---|---|
| | Before administration | 8 weeks after administration | Littermate no treatment mice | 8 weeks after administration | Before administration | 8 weeks after administration |
| 4 week old | 158 | 15 | 16 | 0 | ++ | − |
| 10 week old | 230 | 47 | 19 | 0 | ++ | − |
| 12 week old | 200 | 170 | 35 | 0 | ++ | − |

Figure 2:
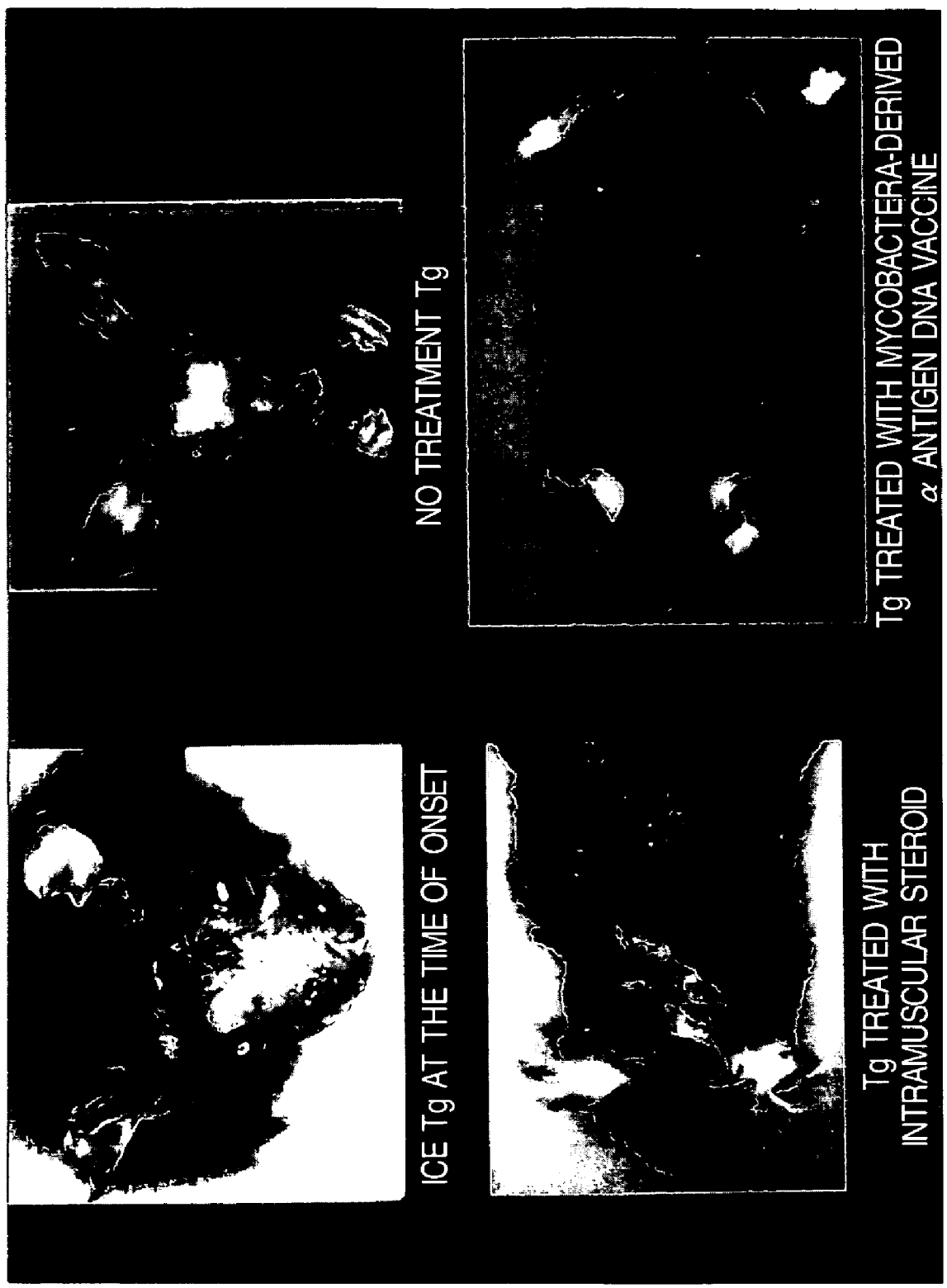
FIG. 2 is a drawing showing the effect of an expression vector containing a gene encoding the α antigen on the treatment of atopic dermatitis.
Figure 3:
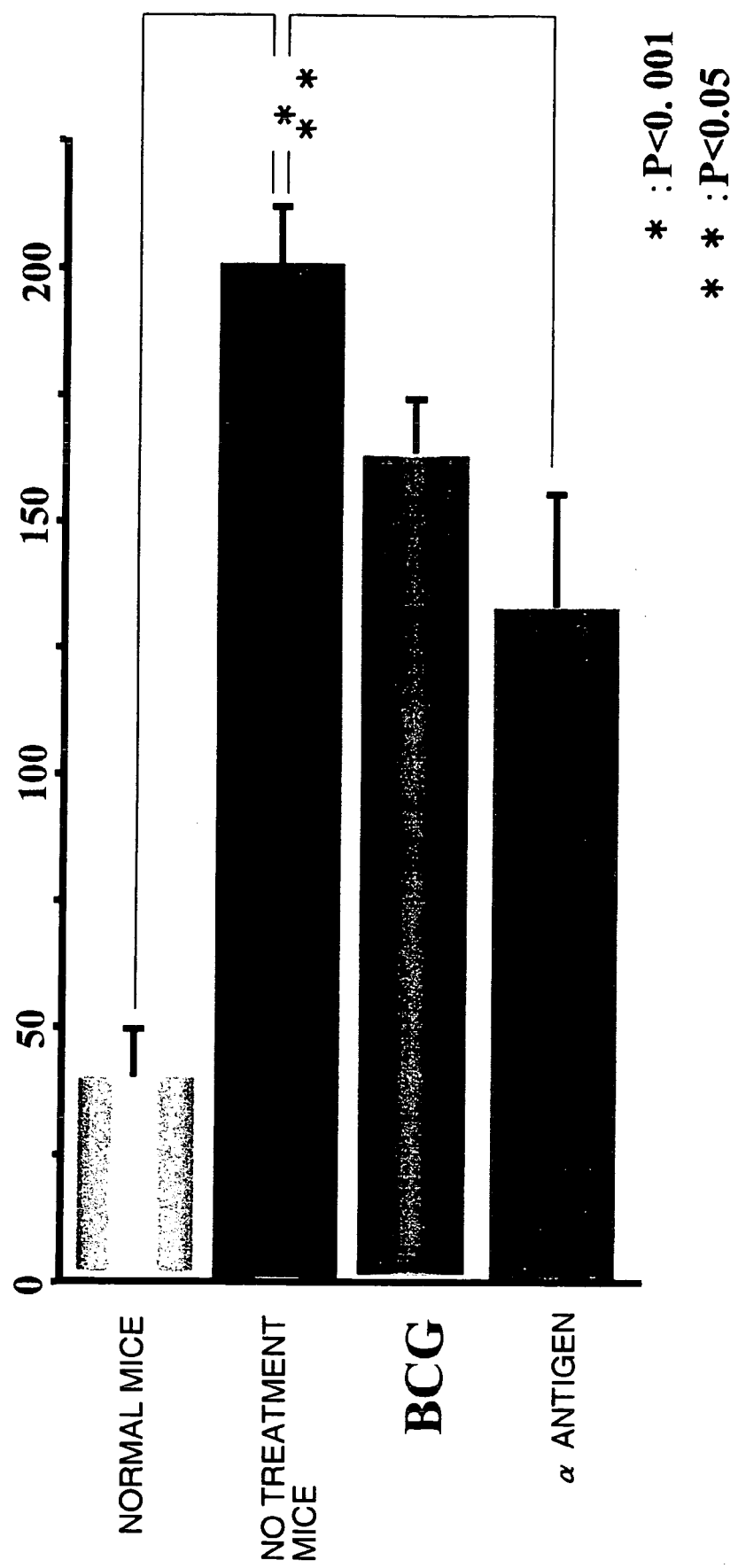
FIG. 3 is a graph showing serum levels of IgE when an expression vector containing a gene encoding the α antigen was administered to a mouse asthma model.
Figure 4:
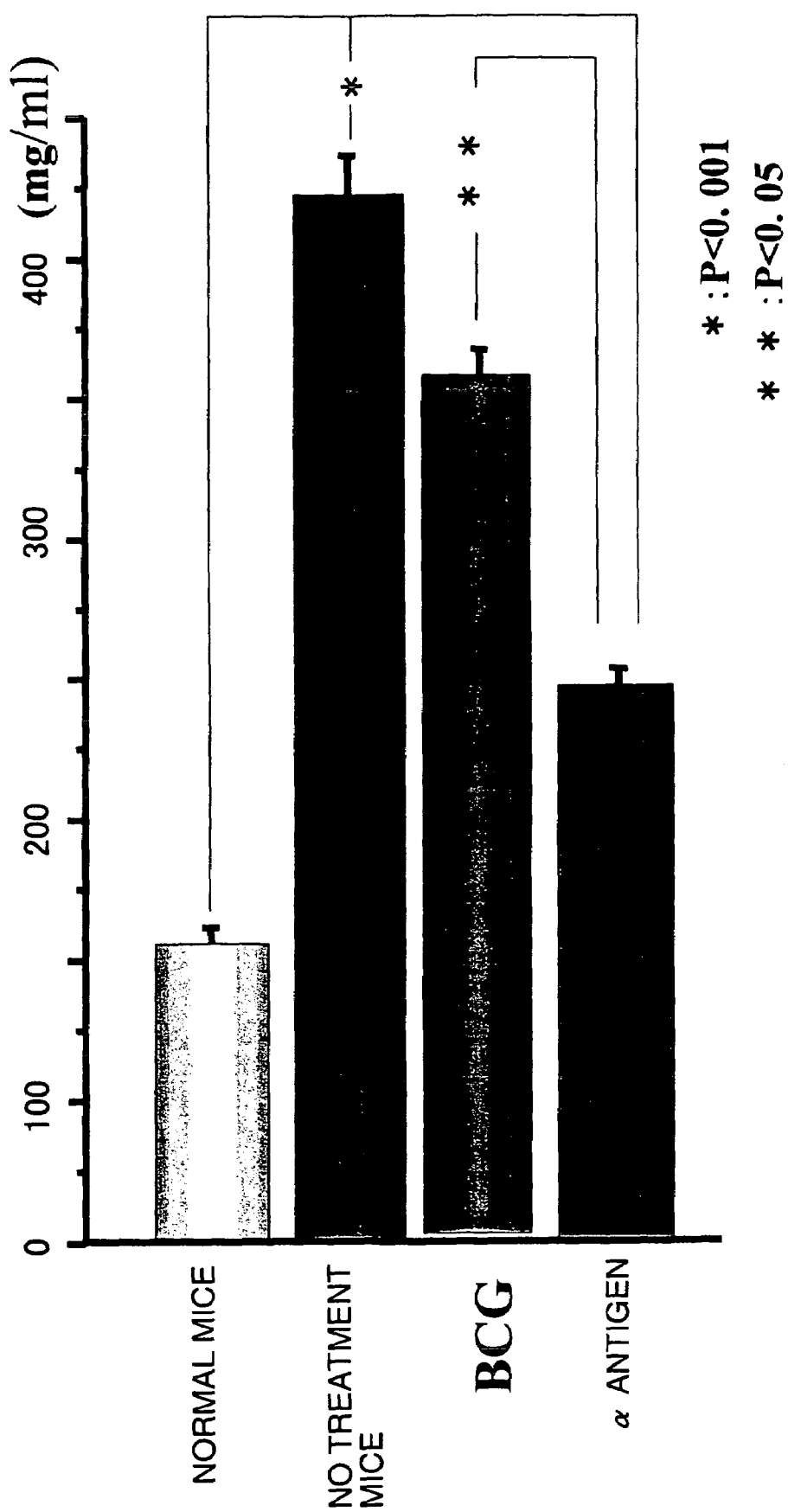
FIG. 4 is a graph showing protein concentrations in the alveolar lavage when an expression vector containing a gene encoding the α antigen was administered to a mouse asthma model.
Figure 5:
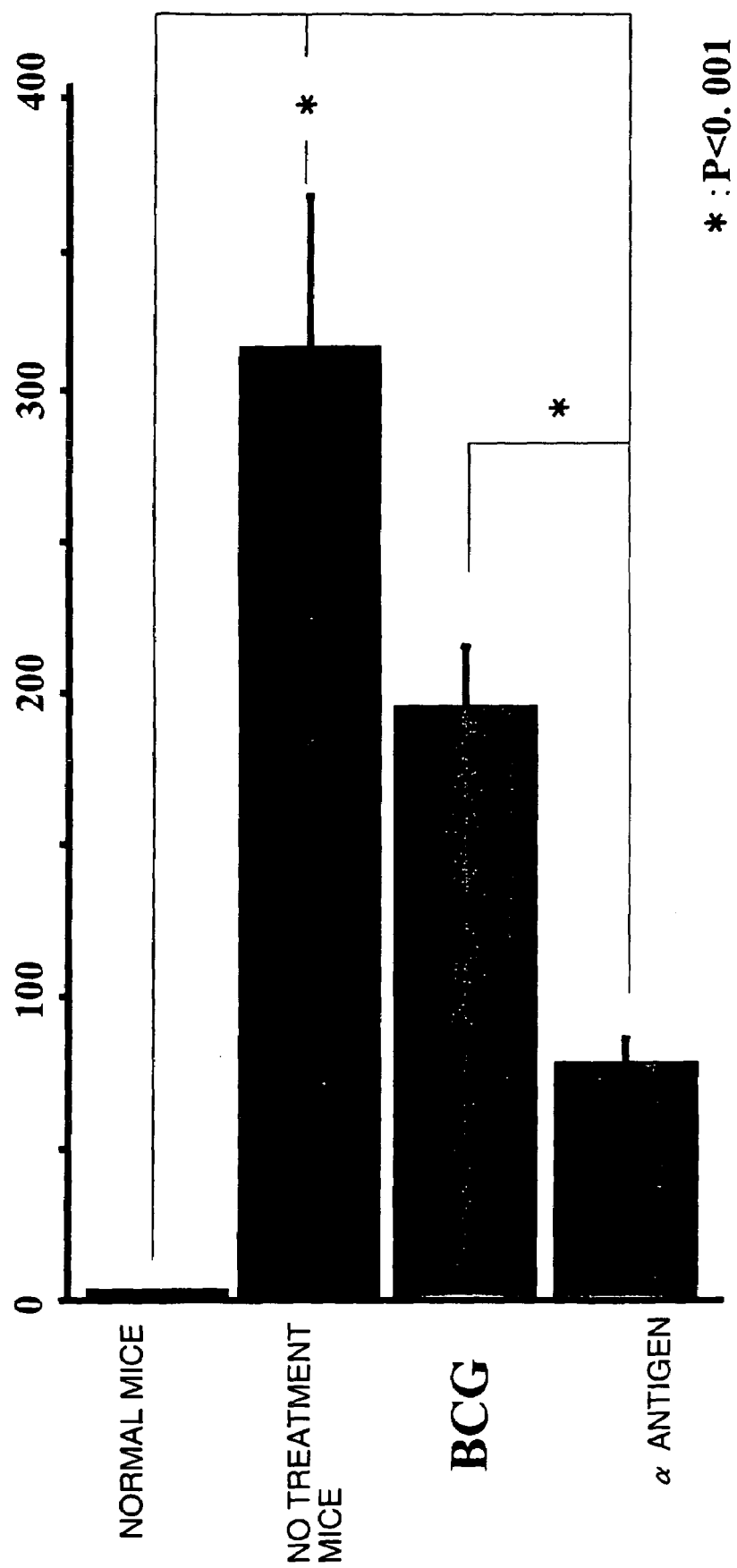
FIG. 5 is a graph showing eosinophil counts in the alveolar lavage when an expression vector containing a gene encoding the α antigen was administered to a mouse asthma model.

In FIG. 2, photographs of various CTg mice are shown. A photograph in top left shows CTg mice at the onset of atopic dermatitis, and one in top right shows 12 week old littermate CTg mice that received no treatment. A photograph in bottom left shows a result in which a littermate CTg mice was cured by the intramuscular injection of prednisolone for 7 days. A photograph in bottom right shows the effect of treatment on week 8 after the intraperitoneal administration of the expression vector constructed in the above (1) to 4 week old CTg mice. After the administration of the expression vector, no development of diseases was seen during the observation period (one year). These photographs clearly indicate that the administration of the expression vector containing the α antigen-encoding gene can very effectively prevent the onset of or treat atopic dermatitis.

EXAMPLE 2

Effect of the α Antigen Protein on Atopic Dermatitis i) Method

Mycobacterium kansasii was cultured in the Sauton medium for 3 weeks, and the culture supernatant was precipitated with 80% ammonium sulfate to prepare a protein fraction. The protein fraction was developed and separated by two dimensional electrophoresis on the gel, and from the corresponding spot on the gel, α antigen protein was extracted and purified (Scand. J. Immunol. 43: 202-209, 1996; J. Bacteriol. 170: 3847-3854, 1988; Hiroshima J. Med. Sci. 32: 1-8, 1983), and dissolved in PBS at a concentration of 1 mg/ml. One μl each of this α antigen protein solution or the control PBS solution was applied on the head of 4 week old CTg mice (N=3 for each) once daily for one week, and then the condition of hair was visually inspected to asses the effect.

ii) Result

When the effect was judged by the amount of remaining hair as + (hair growth is seen) or − (no hair growth is seen), hair on the head was scratched away (due to itching) and the festered skin was exposed (−) in the control to which the PBS solution was only applied, whereas in the α antigen protein-application group hair on the head remained as it was (+to++).

EXAMPLE 3

Effect of Expression Vector Containing the α Antigen-Encoding Gene on Asthma

1) Method

BALB/c mice (N=6 for each group) were immunized with intraperitoneally administration of 10 μg of ovalbumin and 1 mg alum on day 0 and day 14 after the start of the experiment. For five days from day 21, the animals were allowed to inhale aerosol of 5% ovalbumin to create an asthma model. The expression vector (100 μg) constructed in Example 1-(I) and the heated BCG dead organism (100 μg) were intraperitoneally administered in equal amounts, respectively, on day 0 and day 14. On day 25 after the start of the experiment, serum levels of IgE, protein concentration in the alveolar lavage, and eosinophil counts were determined for judgement of effect, and furthermore eosinophil infiltration in the lung tissue was examined by an eosinophil staining (Luna stain). Also the lung tissue was histologically examined.

ii) Result

Serum levels of IgE, protein concentration in the alveolar lavage, eosinophil counts, eosinophil infiltration, and the histological image of the lung are shown in FIG. 3 to FIG. 7, respectively. As can be seen from the result in FIG. 3, serum levels of IgE significantly decreased in the α antigen gene-containing expression vector administration group compared to the no treatment group. As can be seen from the result in FIG. 4, protein concentration in the alveolar lavage which is an index of inflammatory reaction was apparently low in the expression vector administration group compared to the no treatment group and the BCG administration group. As can be seen from the result in FIG. 5, in the expression vector administration group, the number of eosinophils that infiltrate the lung lavage was apparently repressed and the effect was more pronounced than the BCG administration group. As can be seen from the result in FIG. 6, infiltration of a large number of eosinophils was seen in the no treatment group, but not in the expression vector administration group. As can be seen from the result in FIG. 7, apparent allergic inflammation was noted in the no treatment group whereas the expression vector administration group exhibited little difference from the normal mice.

From the foregoing, in the α antigen gene-containing expression vector administration group, a marked effect of suppressing asthma symptoms was noted close to the no treatment normal mice, and the effect was considered to be greater than the administration of an equal amount of BCG.

INDUSTRIAL APPLICABILITY

As described above, when the α antigen, an analog thereof, or an expression vector containing the gene encoding those analogs is administered to atopic dermatitis, histamine release is inhibited, and furthermore the production of IgE and interleukin-4 is suppressed, improving skin diseases and thereby exhibiting a highly effective effect for the treatment of atopic dermatitis. Furthermore, the α antigen, an analog protein thereof or an analog protein thereof also exhibits highly effective effect for the treatment of atopic dermatitis. The α antigen, an analog protein thereof or an analog protein thereof is considered to exhibit the effect of improving the Th2 type cytokine-dominant immunological state, and therefore the α antigen, an analog thereof or the gene encoding an analog thereof, and the α antigen protein, an analog protein thereof or a mutant protein thereof is very effective for the prevention or treatment of atopic diseases such as atopic dermatitis, asthma, allergic rhinitis and allergic conjunctivitis, and more broadly allergic diseases.

The invention claimed is:

1. A method for treating atopic dermatitis or asthma comprising administering to a mammal in need of such treatment an effective amount of an expression vector comprising a polynucleotide sequence encoding the α antigen of *Mycobacterium kansasii* having the amino acid sequence of SEQ ID NO: 2.

2. The method according to claim 1, wherein said mammal is a human.

3. The method according to claim 1, wherein alveolar eosinophil infiltration in said mammal is decreased.

* * * * *